United States Patent
Kertzman

(10) Patent No.: US 7,753,991 B2
(45) Date of Patent: Jul. 13, 2010

(54) WATER TRANSPORT METHOD AND ASSEMBLY INCLUDING A THIN FILM MEMBRANE FOR THE ADDITION OR REMOVAL OF WATER FROM GASES OR LIQUIDS

(75) Inventor: Jack Kertzman, Boca Raton, FL (US)

(73) Assignee: Kertzman Systems, Inc., Boca Raton, FL (US)

(*) Notice: Subject to any disclaimer, the term of this patent is extended or adjusted under 35 U.S.C. 154(b) by 1422 days.

(21) Appl. No.: 11/158,210

(22) Filed: Jun. 21, 2005

(65) Prior Publication Data

US 2006/0021615 A1 Feb. 2, 2006

Related U.S. Application Data

(60) Provisional application No. 60/592,317, filed on Jul. 30, 2004.

(51) Int. Cl.
*B01D 53/22* (2006.01)
*A61M 15/08* (2006.01)

(52) U.S. Cl. .......................... 95/52; 96/4; 96/7; 96/11; 96/14; 128/203.22; 128/204.18; 128/205.27; 128/207.18; 261/104; 261/107; 210/321.75; 210/321.84; 210/500.27; 210/500.41; 73/863; 73/863.21; 73/863.23

(58) Field of Classification Search ............... 95/45, 95/52; 96/4, 7, 14, 11; 128/203.22, 204.18, 128/207.27, 207.18, 205.27; 261/104, 107; 210/321.75, 321.84, 500.27, 500.41; 73/863, 73/863.21, 863.23
See application file for complete search history.

(56) References Cited

U.S. PATENT DOCUMENTS 3,735,559 A 5/1973 Salemme (Continued)

FOREIGN PATENT DOCUMENTS

GB 2 308 988 A * 7/1997

OTHER PUBLICATIONS

DuPont Nafion PFSA Membranes N-112, NE-1135, N-115, N-117, NE-1110 Perfluorosulfonic Acid Polymer, NAE101, Feb. 2004, 4 pages.*

(Continued)

*Primary Examiner*—Jason M Greene
(74) *Attorney, Agent, or Firm*—Laurence A. Greenberg; Werner H. Stemer; Ralph E. Locher

(57) ABSTRACT

A water transport assembly, is provided including a housing having a first chamber therein, which is accessible through an opening in the housing. The housing additionally includes a sample inlet port and a sample outlet port, both of which are in fluid communication with the first chamber. A flat ion exchange membrane is attached to the housing in a plane over the opening in the housing, to seal the opening in a vapor tight seal. Water will pass through the membrane based upon the vapor pressure on each side of the membrane, to either dry or humidify sample passing through the first chamber. When the flat ion exchange membrane is a flat, thin ion exchange membrane it is preferable that the thin ion exchange membrane have a thickness of between about 0.1 and about 3.0 mils.

38 Claims, 10 Drawing Sheets

U.S. PATENT DOCUMENTS

| | | | | |
|---|---|---|---|---|
| 4,612,019 | A * | 9/1986 | Langhorst | 95/52 |
| 4,705,543 | A | 11/1987 | Kertzman | |
| 4,783,201 | A * | 11/1988 | Rice et al. | 95/52 |
| 4,808,201 | A | 2/1989 | Kertzman | |
| 4,846,977 | A | 7/1989 | De Vellis et al. | |
| 5,067,971 | A | 11/1991 | Bikson et al. | |
| 5,084,073 | A * | 1/1992 | Prasad | 95/52 |
| 5,160,511 | A * | 11/1992 | Lovelock | 95/52 |
| 5,182,022 | A | 1/1993 | Pasternak et al. | |
| 5,233,996 | A | 8/1993 | Coleman et al. | |
| 5,411,662 | A | 5/1995 | Nicolas, Jr. et al. | |
| 5,501,212 | A | 3/1996 | Psaros | |
| 5,620,500 | A | 4/1997 | Fukui et al. | |
| 5,693,122 | A * | 12/1997 | Berndt | 96/6 |
| 5,824,919 | A | 10/1998 | Hansen | |
| 5,996,976 | A * | 12/1999 | Murphy et al. | 261/104 |
| 6,042,634 | A | 3/2000 | Van Tassel et al. | |
| 6,048,383 | A * | 4/2000 | Breault et al. | 95/52 |
| 6,145,588 | A | 11/2000 | Martin et al. | |
| 6,171,374 | B1 * | 1/2001 | Barton et al. | 95/52 |
| 6,346,142 | B1 | 2/2002 | Jetter et al. | |
| 6,478,026 | B1 * | 11/2002 | Wood | 128/207.18 |
| 6,523,538 | B1 | 2/2003 | Wikefeldt | |
| 6,610,122 | B1 * | 8/2003 | Filburn et al. | 95/52 |
| 6,635,104 | B2 | 10/2003 | Komkova et al. | |
| 6,655,385 | B1 * | 12/2003 | Curti et al. | 128/207.18 |
| 6,692,556 | B2 | 2/2004 | Hayes et al. | |
| 6,769,431 | B2 | 8/2004 | Smith et al. | |
| 7,357,830 | B2 * | 4/2008 | Weidmann | 95/52 |
| 7,435,284 | B2 * | 10/2008 | Piccinini et al. | 95/52 |
| 2007/0151447 | A1 * | 7/2007 | Merkel | 95/52 |

OTHER PUBLICATIONS

DuPont™, "Nafion® PFSA Products, Perflourosulfonic acid polymer, NAE301" (Feb. 2004), NC, pp. 1-4.

DuPont™, "Nafion® PFSA Membranes, N-112, NE-1135, N-115, N-117, NE1110," Perflourosulfonic acid polymer, NAE101 (Feb. 2004), NC, pp. 1-4.

DuPont™, "Nafion® PFSA Membranes, NRE-211 and NRE-212," Perflourosulfonic acid polymer, NAE201 (Feb. 2004), NC, pp. 1-6.

DuPont™, "Nafion® PFSA Polymer Dispersions, DE 520/521, DE 1020/1021, DE 2020/2021," Perflourosulfonic acid polymer, NAE103 (May 2004), NC, pp. 1-2.

Perma Pure Products, Inc., "Multi-Tube Dryer-Model PD," Bulletin 105, 1 pg.

Perma Pure Products, Inc., "Mini-Dryers-Model MD," Bulletin 106, N.J., 4 pgs.

Dowex Ion Exchange Resins, Dowex Resins as Organic Solvent Desiccants.

* cited by examiner

WATER TRANSPORT METHOD AND ASSEMBLY INCLUDING A THIN FILM MEMBRANE FOR THE ADDITION OR REMOVAL OF WATER FROM GASES OR LIQUIDS

PRIORITY

The present application claims priority from U.S. provisional patent application Ser. No. 60/592,317, Filed on Jul. 30, 2004 and entitled MEMBRANE FOR ADDITION OR REMOVAL OF WATER FROM GASES OR LIQUIDS.

BACKGROUND OF THE INVENTION

1. Field of the Invention

The invention relates to an assembly and method, including a thin film membrane, and more particularly to an assembly using a thin film membrane which is used to humidify or dehumidify a sample gas or liquid.

2. Description of the Related Art

Previously known dryers have used hygroscopic ion exchange membrane tubes in a continuous drying process to selectively remove water vapor from mixed gas streams. Previous known membranes in such dryers have been formed as an extrudible desiccant in tubular form. A single tube, or a bundle of tubes 16 with a common header 18 as shown in Prior Art FIG. 11, is fabricated in a shell and tube configuration and sealed into an impermeable shell 10, which has a wet feed inlet 12 for the introduction of wet product and a dry product outlet 14. Bundles of the tubes 16, each having a wall thickness of between 3-7 mils, may be secured in place using a thermoset resin. A wet gas stream flows through the tubes, while a countercurrent dry gas stream, introduced through the dry purge inlet 20 and evacuated as wet purge gas through the wet purge gas outlet 22, purges the shell. Water vapor molecules are transferred through the walls of the tubing. As a result, the wet gas is dried, and the dry purge gas becomes wet as it carries away the water vapor. U.S. Pat. No. 5,160,511 to Lovelock shows one such so-called multi-tube dryer for drying a wet gas. The '511 patent discloses that tubing and membranes made of perfluoroethylene sulphonic acid under the tradename NAFION® by E. I. DuPont de Nemours have been used to add or remove water vapour from gas mixtures or from flowing streams of gas mixtures.

However, the above disclosed systems may be undesirable due to the cost of the extruded tubing used in such systems. Additionally, the thermoset resin used in the multi-tube devices reduces the chemical inertness of the tubes, as such resins have limited chemical resistance to many corrosive materials. Additionally, the multi-tube dryer end seals can crack when exposed to high temperatures and humidity as the tubing expands.

What is needed is an effective dryer that does not require extruded tubing, and as such, which can be fabricated into laminates or composites, rather than "bundles". What is additionally needed is a device which is usable in a chemically inert fashion. What is further needed is a dryer device that reduces the fabrication, material and operating costs permitting the availability of low cost devices. What is additionally needed is a low cost dryer assembly for large process applications. What is further needed is a materials dryer useful in large flow process applications requiring maximum corrosion resistance.

Additionally, gas humidification systems using water permeable membranes are known. U.S. Pat. No. 5,996,976 to Murphy discloses the use of water permeable polymer materials, including perfluoronated sulfonic acid polymer membranes in the form of a tube, sheet or tubulated sheet, that can be saturated with water to allow evaporation of water into a gas stream passing over a water permeable member. One such procedure for using such tubing to humidify gases and hydrophobic liquids is additionally disclosed in Kertzman, ISA AID 75415 (1975).

An article by the present inventor, published in 1976 describes an apparatus for humidity generation, wherein liquid water at constant temperature is circulated through a tube pack contained in a shell, as with the device shown in FIG. 11. That article, entitled "Humidity Generator II", refers to the energy input required to produce constant humidity. For example, in that article, a means of calibrating the Humidity Generator is described herein temperature sensors are placed at the water inlet and outlet of the tube pack. The inlet temperature measures the water temperature before evaporation of water, and the outlet temperature measures the decrease in temperature due to the latent heat of vaporization for a given mass of water. The water evaporated is calculated from a given formula.

What is further needed is a system for precisely humidifying gases and hydrophobic liquids.

SUMMARY OF THE INVENTION

It is accordingly an object of the invention to provide a water transport method and assembly including a thin film membrane for the addition or removal of water from gases or liquids, which overcomes the above-mentioned disadvantages of the heretofore-known devices and methods of this general type and which.

More particularly, in one embodiment of the present invention, a water transport assembly, is provided including a housing having a first chamber therein, which is accessible through an opening in the housing. The housing additionally includes a sample inlet port and a sample outlet port, both of which are in fluid communication with the first chamber. A flat (i.e., planar) ion exchange membrane is attached to the housing in a plane over the opening in the housing, to seal the opening in a vapor tight seal. Water will pass through the membrane based upon the vapor pressure on each side of the membrane, to either dry or humidify sample passing through the first chamber. In one particular embodiment of the invention, flat ion exchange membrane is thin ion exchange membrane of between about 0.1 and 3.0 mils in thickness.

In one particular embodiment of the present invention, wherein the water transfer assembly is used as a dryer, a regenerable desiccant and/or purge gas are used to draw water through the membrane and out of a sample passed from the sample inlet to the sample outlet, through the first chamber.

In another particular embodiment of the present invention, wherein the water transfer assembly is used as a humidifier, a regenerable desiccant and/or purge gas are used to draw water through the membrane and into a sample passed from the sample inlet to the sample outlet, through the first chamber.

Other features, methods and objects which are considered as characteristic for the invention are set forth in the appended claims.

Although the invention is illustrated and described herein as embodied in a water transport method and assembly including a thin film membrane for the addition or removal of water from gases or liquids, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 12:
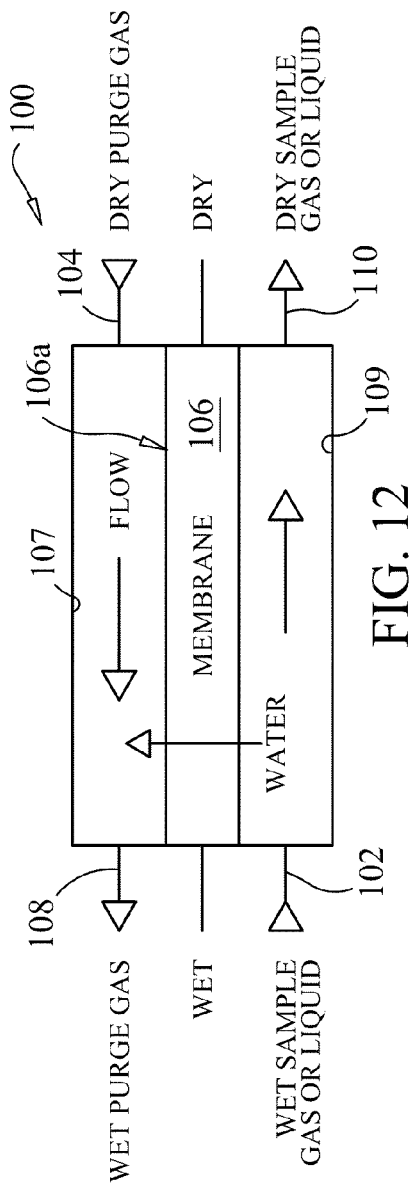
FIG. 12 is a simplified partial cross-sectional diagram of a water transport assembly in accordance with one embodiment of the present invention.

Referring now to the figures of the drawing in detail and first, particularly, to FIG. 12 thereof, there is shown a diagram representing the transport of water through a membrane dryer assembly 100, in accordance with one embodiment of the present invention. As shown in FIG. 12, a wet sample gas or liquid is introduced to a first channel or cavity 109, via the wet sample inlet 102 on a first side of the assembly 100. A dry purge gas is introduced to a second channel or cavity 107, via a dry purge gas inlet 104 at the other or opposite side of the assembly 100. The dry purge gas is introduced via the gas inlet 104, so as to run countercurrent to the wet sample gas or liquid introduced from the inlet 102. The actual flow of dry purge gas should be greater than the actual flow of the wet gas or liquid flow. The assembly 100 contains a flat/planar membrane 106 secured to the assembly's housing in a plane between the first channel or cavity 109 and the second channel or cavity 107, located on opposite sides of the membrane 106 and adjacent the membrane 106.

When using an ion exchange membrane 106 including a sulfonic acid group, it has been found that the driving force in such a water transport assembly is the water vapor pressure gradient, and not the total pressure. Using such a membrane 106, any gas that associates strongly with sulfuric acid will permeate through the ion exchange membrane 106, based on the chemical affinity between water and sulfuric acid. It is not necessary to supply the sample under pressure or to supply a vacuum to the outside of the membrane 106 in order for it to transport water through the membrane 106. As such, a sulfonic acid type membrane 106 can dry gases even when it is at lower pressure than its surroundings. Water transport depends upon on which side of the membrane 106 the gas vapor is more wet. More particularly, the water vapor pressure of the dry purge gas, in such a system, must be lower than the water vapor pressure on the purge side on the surface of the membrane, so that there is continuous evaporation of water from the membrane. The water vapor pressure of the membrane on the wet feed side must be lower than the water vapor pressure of the wet gas or liquid, in order for the membrane to continuously adsorb water from the gas or liquid. As such, if the gases on a first side (for example, chamber 109 of FIG. 12) of the membrane 106 contain more water (i.e., have a higher water vapor pressure) than on the other, second side (in this example, chamber 107 of FIG. 12), the water vapor will move to the second side (i.e., chamber 107). If the gases on the second side of the membrane 106 contain more water (for example, in water bath 128 of FIG. 13), water vapor will move to the first side (i.e., chamber 122 of FIG. 13) which allows the water transport assembly to act as a humidifier rather than as a dryer.

Temperature control of the dry purge gas, wet sample gas or liquid, and the membrane is important in controlling the water vapor pressure of all three, and it can be used to increase or decrease the water vapor pressure of each.

The housing of the assembly 100, and any other embodiment of the present invention, can be made from an inert material, such as inert (non-hygroscopic) thermoplastics, fluorocarbons, coated fluorocarbons or chemical resistant metals. Inert thermoplastics that provide sealable connections to other inert plastics, fluorocarbons, coated fluorocarbons or chemical resistant materials are preferred. Additionally, the housing of the assembly 100, or any other embodiment of the present invention, unless otherwise specified, can be any shape, such as a square, a rectangle or circular in shape. It is desirable to keep the internal volume or space between the filters, membranes, sample and purge internal volume to a minimum. Such small volumes are used to create rapid transport of water across the membrane.

A wide range of fittings or connectors can be used to introduce the wet sample and purge gas to the inlets 102 and 104, respectively. For example, a variety of barbed, luer and/or compression fittings, may be used. Alternatively, some or all of the fittings may be molded into, or as part of, the dryer assembly housing. Optionally, the dryer assembly housing may contain male/female screw connections or special male/female connections that interact with special low volume mating connections.

Optionally, baffles may be formed in the internal volume and/or other materials may be placed in the internal volume to help make intimate contact between the fluids and the membrane, and to provide turbulence and prevent channeling of the sample and purge gas. If added, it is preferable that the other materials be inert non-hygroscopic materials.

For purposes of the present invention, the membrane 106 has been chosen to have certain characteristics. More particularly, it is desired that the membrane 106 have a low equivalent weight, such as an equivalent weight ("EW") on the order of between 850 and 1100. Additionally, it is desired that the membrane 106 include a thin ion exchange film or dispersion of preferably between about 0.1 and 3.0 mils in thickness. "About", when used in terms of the present thicknesses, can mean as much as +/−10%, unless otherwise specified. More preferably, the membrane is between about 0.1 and 2.0 mils. Most preferably, the thin ion film membrane is less than about 1.0 mils.

In a preferred embodiment, the membrane 106 is made of a sulfonic acid membrane polymer or ionomer, such as a perfluorosulfonic acid polymer made under the NAFION® tradename by DuPont™. Other membranes of the sulfonic acid type, that produce rapid and selective water transport can be used with the instant invention. Such sulfonic acid type membranes additionally include, but are not limited to: per-sulfonic acid membranes made by DuPont™, the Dow® Chemical Company (low E.W.), Asahi Glass Co., Ltd., and Asahi Chemical Industry Company; grafted divinyl benzene sulfonic acid on polyolefins or fluorocarbon films; Trifluoro stryrene and ethylene styrene interblend sulfonic acid from Dow™ resins; polybenzimidazole (PBI) sulfonic acid from Celanese Ventures Gmbh of Frankfurt, Germany and Ballard Fuel Cells, Inc.; and polyarylether or polyetherether ketone (PEEK) sulfonic acid from Victrex® PLC. Any of the above types or other similar types of sulfonic acid polymers may be used in the present invention where ever an ion exchange membrane, such as a NAFION® membrane, is disclosed.

Additionally, the sulfonic acid type ion exchange membrane used with the present invention can be converted to the hydrogen form to deliver the highest water transport rate. As such, it is most preferred to use NAFION® membranes in the acid (H+) form. NAFION® membranes, known as N-112, NE-1135, N-115, N-117 and NE-1110 made by DuPont™ have been made which are non-reinforced films based on NAFION® PFSA polymer, a perfluorosulfonic acid/PTFE copolymer in the acid (H+) form. NAFION® membranes, known as NRE-211 and NRE-212 by DuPont™, have been made which are non-reinforced dispersion-cast films based on NAFION® PFSA polymer. Other cationic or anionic forms of thin ion exchange films may be used, but may produce lower water transport rates. Additionally other types of sulfonic acid type polymers can be used and, similarly, converted to the H+ form. For example, a converted vinylbenzylchloride (VBC) polymer, such as made by the DOW® Chemical Company could be used as a film or on a porous inert sheet or screen. When the NAFION® material is used in the present invention, the inertness of TEFLON® (TFE) is combined with a sterically isolated sulfonic acid group to produce a membrane that permits energy efficient separation of water from high value gases and liquids. Composites of a sulfonic acid type ion exchange film can additionally be made, using the thinnest ion exchange film, but control of the thickness and uniformity of the coating may vary more than with cast film.

Figure 14:
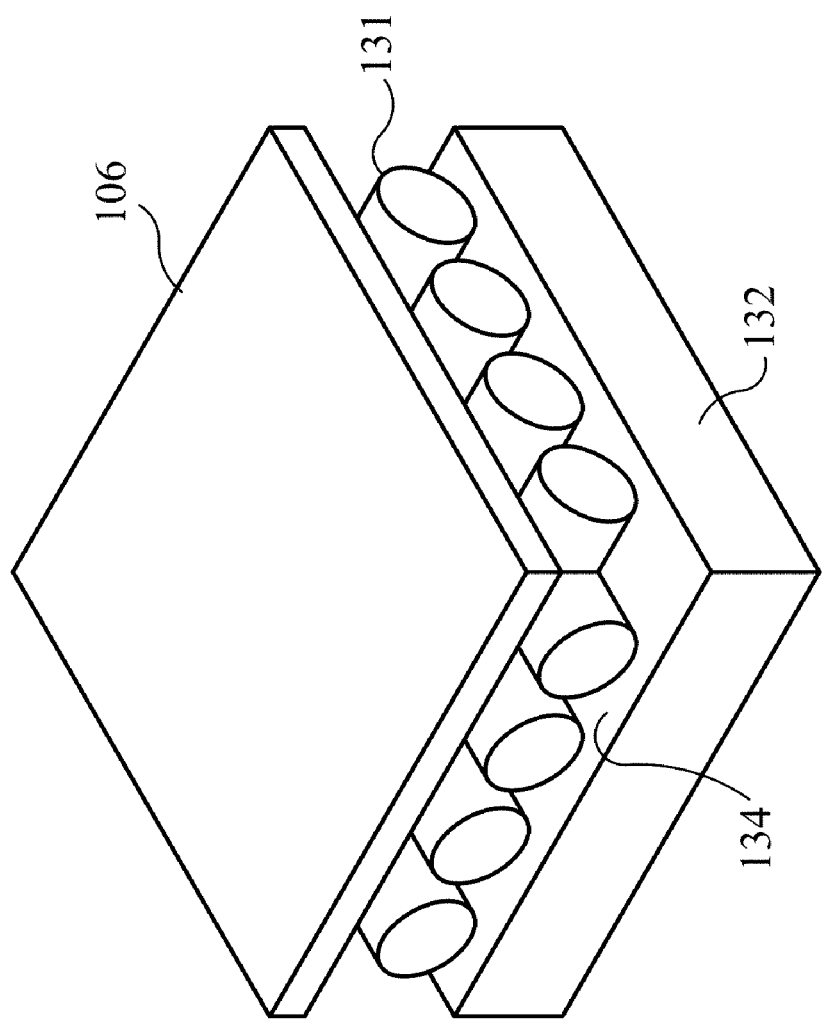
FIG. 14 is an isometric view of a partial rectangular cross-sectional portion of a water transport assembly including a flat/planar thin ion exchange membrane mounted over a cavity containing in a housing, which cavity includes a portion of a screen in accordance with an embodiment of the present invention.

In systems using low pressure gas or liquid samples, the thin ion exchange film can be unsupported or bare, depending on the membrane dimensions. However, in accordance with the present invention, the thin ion exchange film, may be supported on a laminated material, such as an inert metal or plastic screen or a thin, porous film. Additionally, a supported membrane may be formed by coating a porous inert sheet with a solution of the ion exchange dispersion. The laminated material adds mechanical strength to the thin membrane and may help increase the turbulent interaction of the wet gas or liquids and the purge gas. For example, referring to FIG. 14 of the present invention, there is shown an isometric view of a cut-away of a portion of the housing 132 including the chamber 134 having an inert screen 131 therein, which can be used to increase the turbulent interaction of the wet gas and the purge gas. The inert screen 131 is located in the chamber 134, below the flat/planar membrane 106. Additionally, corrosion resistant metal screening or porous metal can be used to provide better heat transfer to the membrane than plastic, as the metal has a higher conductivity.

Additionally, several thin thermoplastic screens (such as inert screen 131 of FIG. 14) or porous plastic or metal membranes (not shown) can be mounted in the dryer 100 enclosure to protect the membrane against contamination from solids and condensable liquids. These filters may be used in the bypass mode to continually remove solids and condensable liquids, or in a dead end alignment where there is a minimum contamination of the sample.

Note that when it is stated that the ion exchange film or dispersion on a porous sheet is, preferably, between 0.1 and 3.0 mils in thickness. The thickness of any, optional, laminated material or filter screens is not included in this preferred measurement. Additionally, seals between the membrane, laminates, composites and/or filters may be made with thin non-hygroscopic polymers or elastomers.

Referring back to FIG. 12, the purge gas in the channel 107 draws the water from the channel 109 through the membrane 106, such that, wet purge gas exits the assembly 100 from a purge gas outlet 108 at the "wet side" of the assembly 100. Similarly, dry sample gas or liquid (i.e., with the water removed) exits the channel 109 from the sample gas outlet 110, on the "dry side" of the assembly 100. Note that at the "dry side" of the assembly 100, the membrane 106 is additionally dry, and at the "wet side", the membrane 106 is wet. Within the assembly 100, there is a water concentration along the horizontal plane of the membrane, as well as a gradient through the membrane thickness, as one side of the membrane is adsorbing the water and the other is evaporating the water. The heat of adsorption at the membrane 106 is offset by the cooling from the latent heat of vaporization from the evaporation of water at the other side of the membrane 106. It should be noted that the above described mechanism of the present invention is different from the reactions that take place by drying with solid desiccants, wherein the heat of adsorption is carried out, as heat, with the dry products. Such solid desiccants, once wet, then require heat and dry purge gas to remove the adsorbed water during their regeneration. Note however, if low humidity purge gas is not available, a dry desiccant may be placed in contact with the surface 106a of the dry membrane 106. As will be described further below in connection with additional embodiments, instead of exposing this surface 106a to ambient humidity, a small quantity of solid dry desiccant may be placed in an enclosed chamber and exposed to the membrane surface opposite the membrane 106's wet face. The dry desiccant can be separated from the membrane surface 106a with a porous netting or plastic. The desiccant may, optionally, contain a humidity indicating material to indicate the drying performance of the desiccant.

Additionally, as noted above, the dryer of the present invention works with wet sample gases or liquids. However, drying wet hydrophobic liquids requires control of temperature, gas and liquid flow, vacuum pressure and moisture concentrations. The presence of dissolved water in liquids requires calculation of the water concentration based on the volumetric amount of water expressed as weight per volume. Then, to remove the actual volume of dissolved water in hydrophobic liquids requires the calculation of the actual volume of dry gas required to accomplish this. Sufficient dry purge gas must be used to evaporate the adsorbed water passing through the membrane 106. Two variables that can be adjusted to dry these liquids are temperature and pressure. For example, maintaining the membrane 106 and assembly 100 at low temperatures and the purge gas at low vacuum pressure, can help to dry hydrophobic liquids to the level of only a few parts per million (ppm) or parts per billion (ppb). The low pressure of the purge gas helps reduce the partial pressure of water in the purge gas, and increases the volumetric flow by expansion. One low cost material that can be used to adjust the temperature and pressure of the assembly to help dry wet liquid samples is liquid nitrogen. Liquid nitrogen can be vaporized to produce the desired low temperatures, while the vapor can be expanded to provide the necessary actual volumes of dry purge gas to dry the liquids to the desired low water concentrations.

Figure 13:
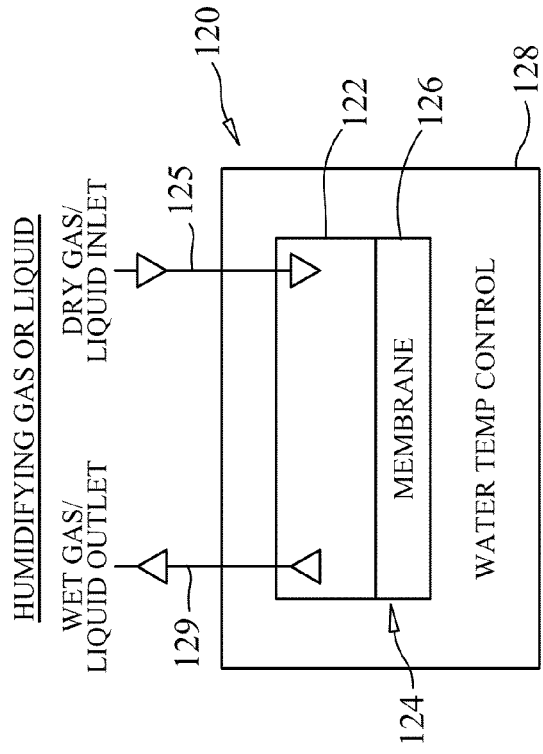
FIG. 13 is a simplified diagram of a humidifying system in accordance with one embodiment of the present invention.

Referring now to FIG. 13, there is shown a humidification assembly 120 for humidifying a gas or liquid. Humidification control requires temperature and flow control of the dry gas and water so that a dry gas can be saturated at the water temperature. The heat or energy input to control the water temperature includes the heat losses by the evaporation of water (latent heat of vaporization) and the heat losses produced by cooling of the container holding the water by conductivity. Further, adsorption of water produces heat, while evaporation of water produces cooling (latent heat of vaporization), simultaneously. A 10 degree C. change in the temperature of the system can double the water transport rate or reduce the water concentration in the dry gas or liquid samples. The energy input to such a system must be balanced to supply heat to raise the water temperature and overcome the cooling from the vaporization of the water.

The humidifying assembly 120 includes a humidifier shell 122 having a membrane 126 attached over a cavity through the body 122. In the preferred embodiment, the membrane 126 is chosen to be a thin ion exchange film membrane of the type described in connection with the membrane 106 of FIG. 12. The membrane 126 is additionally sealed to the shell 122, in a gas tight seal, as described in connection with the device of FIG. 12.

The humidifying device 124, including the shell 122 and membrane 126, is immersed in a temperature controlled water bath 128. A dry gas or hydrophobic liquid sample is introduced through an inlet 125 and run through the cavity of the shell 122, resulting in the humidification of the sample by water molecules that are passed from the water bath, through the membrane 126. The humidified gas or liquid sample exits the humidifier device through the wet gas/liquid outlet 129. Control of humidity level added to the dry sample will depend on the water temperature of the water bath, the membrane surface area and thickness and the flow rate of the sample. Note that, as with the dryer embodiment of FIG. 12, it is desirable to keep the volume of the inner shell cavity to a minimum.

Figure 1:
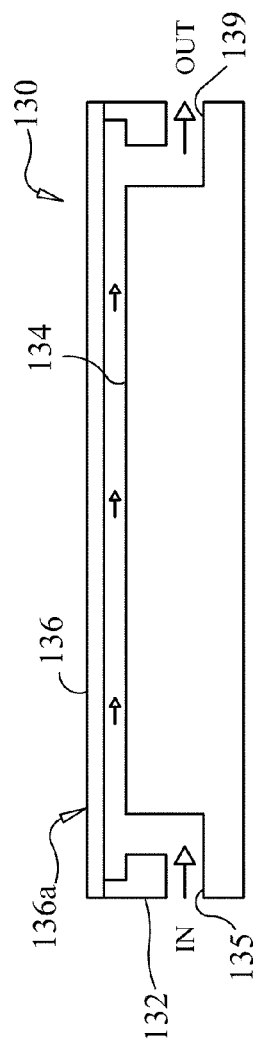
FIG. 1 is a partial cross-sectional diagram of an open-faced ion exchange membrane water transfer assembly in accordance with one embodiment of the present invention.

Referring now to FIG. 1, there is shown a single-faced membrane humidifier/dryer assembly 130, in accordance with one embodiment of the present invention. The assembly 130 includes a shell 132, including a cavity 134. A membrane 136 of the sulfonic acid type is sealed to the shell 132, in a plane over the cavity 134. A sample inlet 135 and a sample outlet 139, provide an inlet and outlet, respectively, for the sample to be dried. Shell 132 can be configured as a square, a rectangle or can be circular in shape. Additionally, the shell 132 can be made of inert non-hygroscopic thermoplastics, such as polyolefins or fluorocarbons, coated fluorocarbons or chemical resistant metals.

It is desired that a low volume be maintained between the bottom of the thin membrane 136 and the bottom of the shell cavity 134. In order to maintain inertness, the edges of the membrane 136 may be heat sealed to the surface of the outer shell 132 to form a gas tight seal. Alternately, the seal between the edge of the membrane 136 and the shell 132 may be formed ultrasonically. If the shell 132 is made from an inert metal, or if another means of securing the membrane 136 is desired, the outer edges of the membrane 136 can be sealed to the shell 132 using mechanical means, such as clamps, screws, inert gaskets and/or elastomeric materials (not shown). Such inert metal shells can be made from a fluorocarbon or electrodeless nickel/fluorocarbon coating over aluminum or stainless steel. If mechanical means are used to secure the membrane 136 to the shell 132, the membrane 136 can be replaced if it becomes contaminated or damaged.

As with the description of the dryer assembly 100, above, the membrane 136 is preferably chosen to have a low equivalent weight, such as an equivalent weight ("EW") on the order of between 850 and 1100, and to include a thin ion exchange film or dispersion of between 0.1 and 3 mils in thickness. Most preferably, the membrane 136 is chosen to be a perfluorosulfonic acid polymer, such as NAFION®, as described in connection with the embodiment of FIG. 12. Additionally, as in that embodiment, the membrane 136 can be encased in a thermoplastic screen or porous covering.

When the assembly 130 is used as a dryer, the upper surface 136a of the membrane 136 is exposed to the ambient air, the dryer 130 will dry the wet sample introduced through the inlet 135 to the same humidity as the ambient air surrounding the dryer 130 (i.e., the humidity in the sample reaches equilibrium with the ambient humidity). Lower humidity samples can be obtained by placing a porous screen on top of the upper surface 136a of the membrane 136, and covering the upper surface 136a with a small open container containing a solid regenerable desiccant, such as silica gel, molecular sieves, alumina or calcium sulfate hemihydrate. The solid regenerable desiccant provides additional drying of the sample.

The assembly 130 can also be used as a humidifier to humidify a dry sample, when used in connection with a water bath, as described in connection with FIG. 13.

Figure 2:
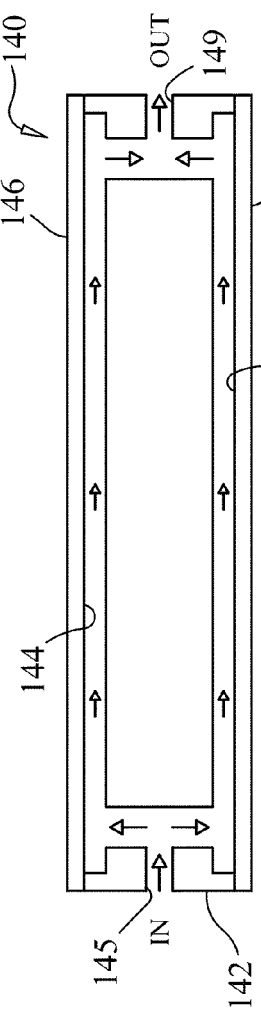
FIG. 2 is a partial cross-sectional diagram of a dual-faced ion exchange membrane water transfer assembly in accordance with another embodiment of the present invention.

Referring now to FIG. 2, there is shown another embodiment of the present invention. The humidifier/dryer assembly 140, is similar to that of humidifier/dryer assembly 130 of FIG. 1, except that the shell 142 has been constructed so as to include two flat/planar membranes 146 adjacent opposite side faces of the dryer housing 142. The opposed membranes 146 are preferably chosen from among those sulfonic acid types described in connection with membrane 106 of FIG. 12 and membrane 136 of FIG. 1. Additionally, the membranes may be formed with additional structural screens, supports, laminates and/or composites, as described in connection with earlier embodiments.

As with the previously described devices, the assembly 140 of FIG. 2 includes an inlet 145 into which the wet sample is diverted, so as to flow into the shell cavities 144, passing both membranes 146 and exiting the outlet 149. But for having two cavities 144 in contact with two membranes 146, instead of one membrane, the assembly 140 is otherwise the same as the assembly 130 of FIG. 1. As such, the options and choices available for the construction and/or supplementation of the assembly 130 would equally apply to the assembly 140.

As with the humidifier/dryer 130 of FIG. 1, the assembly 140 can also be used as a dryer, as described in connection with FIGS. 12 and 1, or, when used in connection with a water bath, as a humidifier to humidify a dry sample, as described in connection with FIG. 13.

Figure 3:
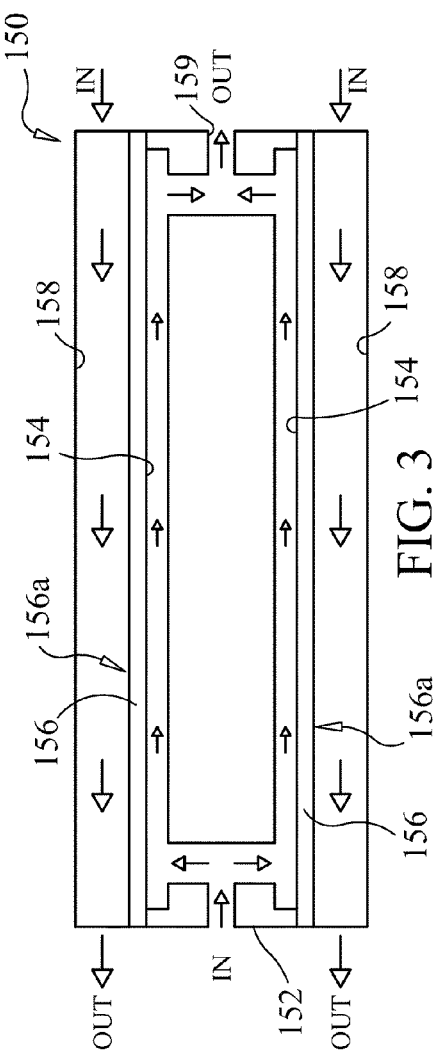
FIG. 3 is a partial cross-sectional diagram of an ion exchange membrane water transfer assembly in accordance with another embodiment of the present invention.

Referring now to FIG. 3, there is shown a dryer assembly 150 in accordance with one embodiment of the present invention. The dryer assembly 150 includes the same base configuration as the assembly 140 of FIG. 2, but further includes purge gas chambers or channels 158 formed in communication with the housing 152. More particularly, when drying a wet sample, dry purge gas running through the purge chambers 158 above the outer faces 156a of the membranes 156 will draw water content from the wet sample, and through the membranes 156. A dry purge gas is introduced to the purge gas channels 158, countercurrent to the flow of the wet sample through the cavities 154. As with the above embodiments, it is preferred that the volume of the cavities 154 be minimized. For example, in one particular embodiment, the depth of the cavity may be only about 5 mils. Additionally, the membranes 156 are thin ion exchange film membranes of the sulfonic acid type, as described in connection with the embodiments of FIGS. 12 and 1. Desirably, the actual volume of purge gas should exceed the actual volume of wet sample gas or liquid introduced to the assembly 150. Alternatively, the wet sample humidity can be reduced using the assembly 150 by placing a solid regenerable desiccant, such as silica gel, molecular sieves, alumina or calcium sulfate hemihydrate into the purge chambers 158. If a solid desiccant is placed into the purge chambers 158, it would be necessary to periodically replace/regenerate the desiccant, as it becomes saturated with the adsorbed water.

Note that the embodiment of FIG. 3 is described in connection with a dryer that includes two membranes 156 located above two housing cavities 154. However, this is not meant to be limiting. From the embodiment shown in FIG. 3, it is understood that the embodiment of FIG. 1, can likewise be adapted to include a purge chamber/channel 158, over a single membrane 156 of the sulfonic acid type, without the second cavity, purge chamber or membrane. As such, from the embodiment shown in FIG. 3, it can be understood how to adapt the single-faced membrane dryer 130 of FIG. 1 to include a purge chamber over the membrane 136.

Figure 4:
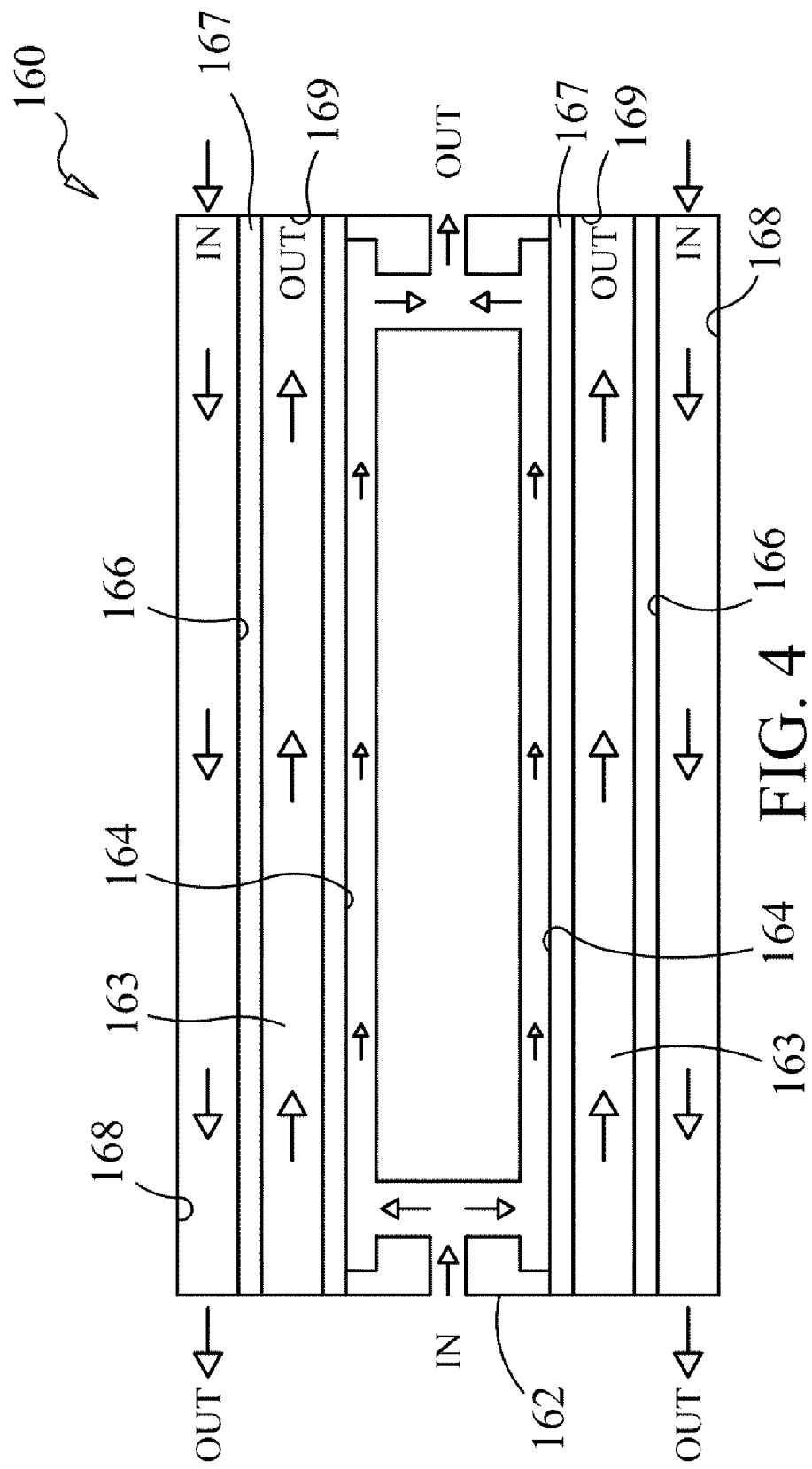
FIG. 4 is a partial cross-sectional diagram of an ion exchange membrane water transfer assembly in accordance with another embodiment of the present invention.

Referring now to FIG. 4, there is shown one embodiment of the present invention including the addition of a bypass filters 167 to the assembly 160. The assembly 160 is similar to the assembly 150 of FIG. 3, in that it includes a housing 162 including the dual cavities 164 in contact with the membranes 166 and purge gas channels or chambers 168. However, the assembly 160 additionally includes the two bypass filters 167. The bypass filters can be composed as described earlier herein. For example, a corrosion resistant, non-hygroscopic fine screen or porous plastic filter is placed in the housing 162, between the wet sample and the lower surface of the membrane 166. As with previous embodiments, all internal dead volumes should be kept to a minimum. All wet samples containing particulates or condensable liquids are passed through the filter dryer in a bypass mode and are removed from the wet sample. The pressure drop across the filter 167 and into the lower surface of the membrane 166 must be kept low. The wet, filtered sample passes through a chamber or cavity 163, containing the membranes 166, and exits from two outlets 169 below the lower surfaces of the membranes 166. Dry purge gas or solid desiccant chambers 168 can be placed above the upper surfaces of the membranes 168 to obtain further water reduction of the wet samples, as described in connection with FIG. 3. Additionally, the housing 162 and thin ion exchange film membranes 166 can be chosen as described in connection with the previous embodiments.

Note that, as with the embodiment of FIG. 3, from the above teachings, it can be seen how the embodiment of FIG. 4 can be adapted for use with a single-faced membrane dryer, such as is shown in connection with FIG. 1.

Figure 5:
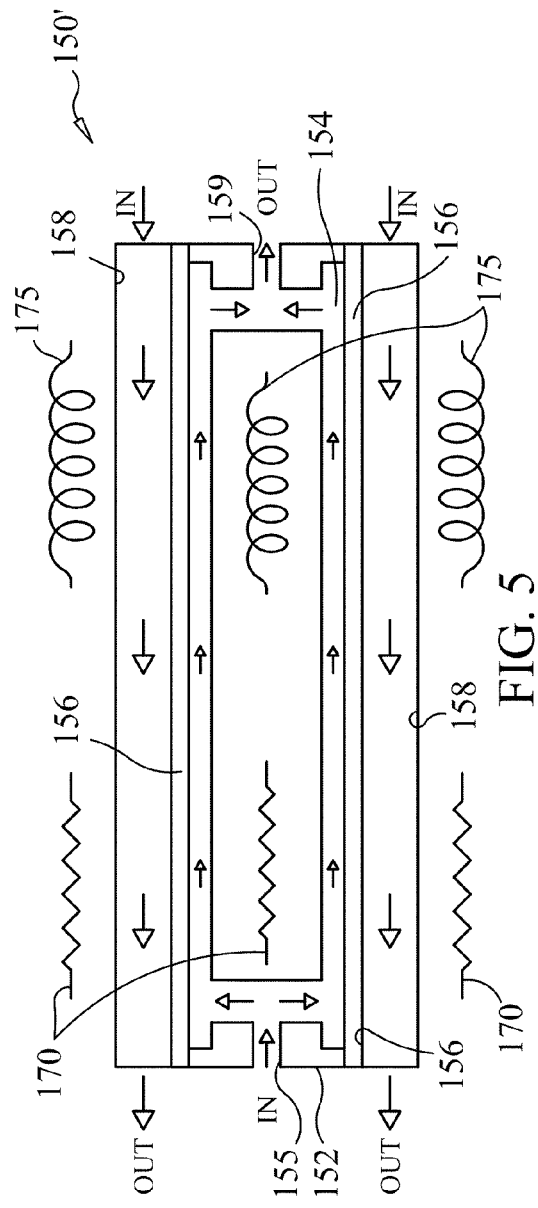
FIG. 5 is a partial cross-sectional diagram of an ion exchange membrane water transfer assembly configured as a dryer, in accordance with another embodiment of the present invention.

As previously described, the drying of certain samples, such as hydrophobic liquids, can be greatly influenced by the temperature of the membrane and assembly, and by the pressure of the purge gas. Referring now to FIG. 5, there is shown one particular embodiment of the present invention including mechanisms that can influence the temperature of the assembly 150'. For purposes of discussion only, the present embodiment including temperature control mechanisms will be described in connection with the embodiment of FIG. 3. This is not meant to be limiting. Note that the use of temperature control devices, such as described in connection with the present embodiment, can be used in connection with any of the embodiments of FIGS. 12 and 1-4.

Referring back to FIG. 5, there is shown a dryer assembly 150' including a housing 152 including membranes 156. Increasing or lowering the temperature of the assembly 150' and/or membranes 156 can effect the removal of water from the sample. For example, water transport can be increased at higher temperatures and lower the water concentration in the dry products. Temperature control mechanisms, such as heaters 170 and/or cooling mechanisms 175, can be added to the assembly 150' and used to raise or lower the temperature of the wet samples in the dryer assembly 150'. As shown in FIG. 5, such heaters 170 and/or cooling mechanisms 175 can be placed in and/or on the gas purge chambers 158 and shell 152. Additionally, if desired, heaters 170 and/or cooling mechanisms 175 can be additionally provided to raise or lower the temperature of the wet sample that are to be introduced to the assembly at the inlet 155, prior to introduction. Although shown with both, if desired only one of heaters 170 and/or cooling mechanisms 175, or a variety of heaters 170 and/or a variety of cooling mechanisms 175, may be used.

However, when drying wet samples, it is desirable to keep the wet sample inlet temperature to at least 10° C. above the wet sample inlet dew point, to prevent condensation of water and to increase evaporation through the membrane 156. Known heating devices, such as inductive or resistive heaters can be used as the heaters 170.

Cooling the dryer assembly 150', membranes 156 and purge chambers 158 can be accomplished by the use of any of a number of cooling mechanisms 175. For example, cooling mechanisms 175 useful with the present invention to achieve greater water reduction in gases and liquids can include thermoelectric or mechanical refrigeration or liquid coolants. Low temperatures reduce the water vapor partial pressure in the membrane 156 so it can adsorb even low water concentration from the wet samples. It is desired that the dry purge gas have a lower water vapor concentration than the membrane, so that the purge gas can remove water adsorbed on the dry membrane surface.

Figure 6:
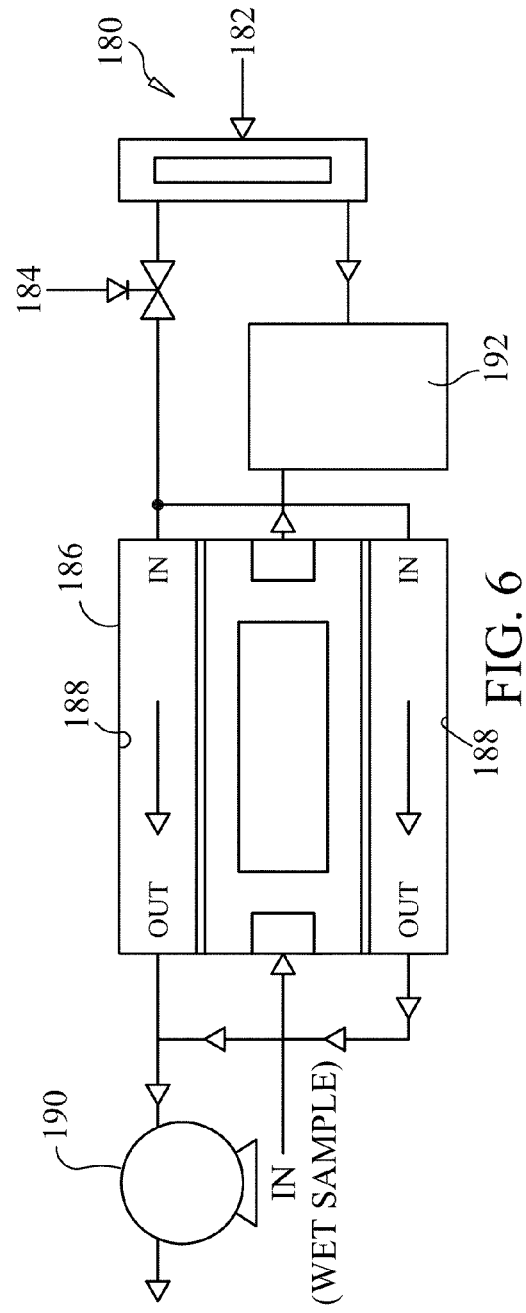
FIG. 6 is shown a diagram of a gas reflux system configured as a dryer, in accordance with another embodiment of the present invention.

Referring now to FIG. 6, there is shown a simple diagram of a reflux system 180 in which a wet sample is dried. In a reflux system, all or part of a dry sample is expanded and is used as the purge gas. In such a system, if the wet sample is a high pressure gas, it can be dried and a portion of it can be used as the purge gas. In the reflux system 180, low or atmospheric pressure samples pass through a flow meter 182 and an expansion valve 184. The expanded dry sample is passed through the purge chambers 188 of a dryer assembly 186. Although a dryer assembly 186, such as the assembly of FIG. 3 is shown, other dryer assemblies in accordance with the present invention can be used in the system 180. A wet sample is additionally introduced into the sample cavity of the dryer assembly 186. The expanded dry sample passes through the purge chambers 188 to a vacuum pump 190. Sample dried in the assembly 180 is provided to a gas analyzer 192, where it is compared with samples from the flow meter 182.

Figure 7:
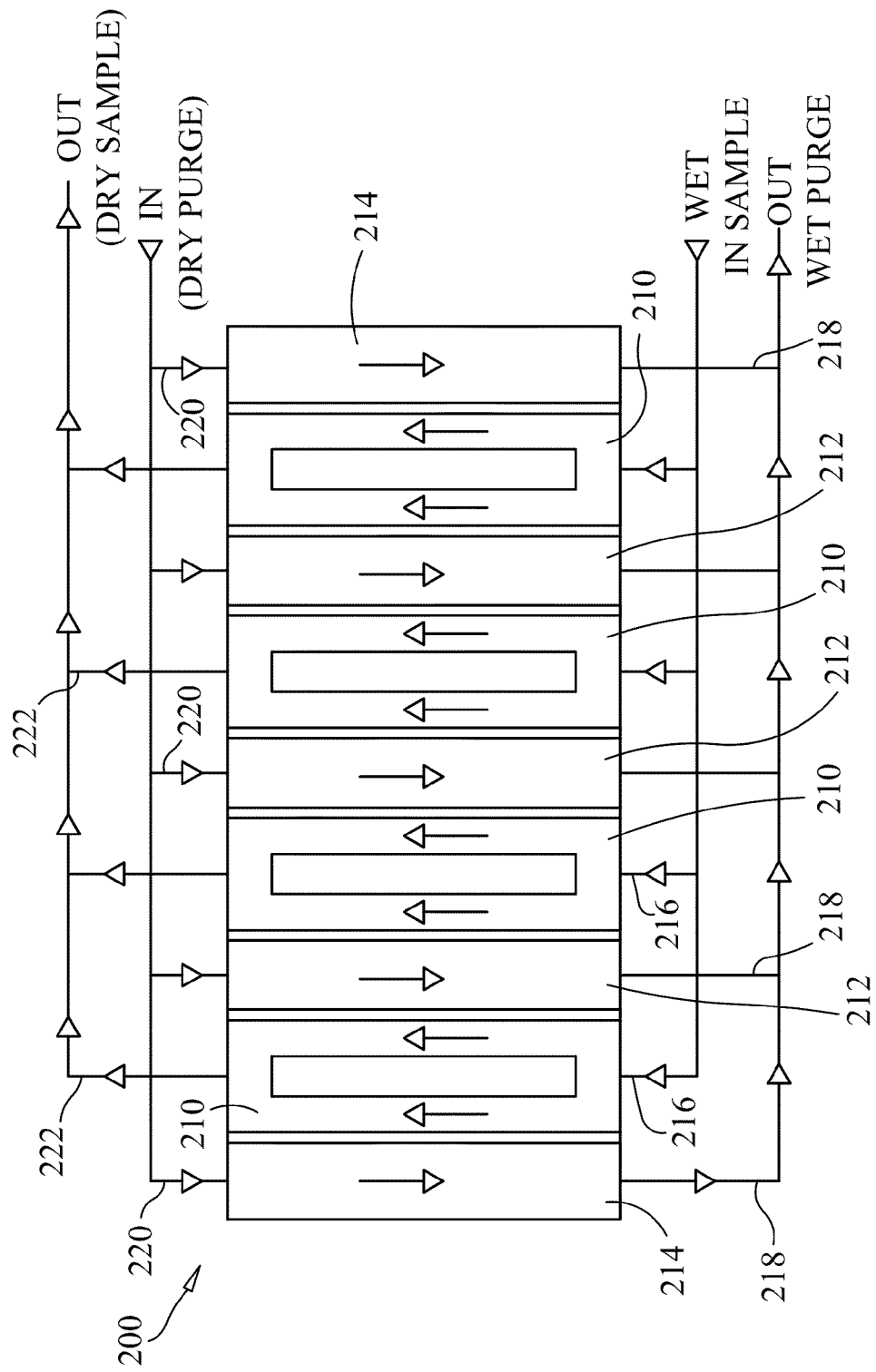
FIG. 7 is a partial cross-sectional diagram of a multiple ion exchange membrane water transfer assembly configured as a dryer, in accordance with another embodiment of the present invention.

Referring now to FIG. 7, there is shown a multiple dryer assembly 200 in accordance with one embodiment of the present invention. When large quantities of wet gas or liquid samples are dried, it may be necessary to line up several double faced membrane dryers 210 in parallel, with double faced purge gas chambers 212 located between them. A single faced purge gas chamber 214 can be placed at each end of the parallel array 200. Wet sample is provided on the wet side of the parallel array 200, via inlets 216 attached to each dryer 210. Wet purge gas exits the parallel array 200 on the wet side from purge gas outlets 218 from each of the purge gas chambers 212, 214. Additionally, on the dry side of the parallel array 200, dry purge gas is introduced through purge gas inlets 220 to the purge gas chambers 212, 214, while dry sample exits from each dryer 210 through the dry sample outlets 222. Note that, although FIG. 7 shows a single source of wet sample and/or purge gas, multiple sources of wet sample and/or purge gas can be connected to the inlets 216 and/or 220, respectively.

A temperature gradient may be used in connection with the parallel array 200 to reduce the water in the wet sample. A 10° C. drop in the dryer system temperature will double the water reduction in the wet product. Efficiencies, as previously described, can be achieved by controlling the temperature, flows, pressure, vacuum and measurement of the water concentration throughout the parallel array 200.

Figure 8:
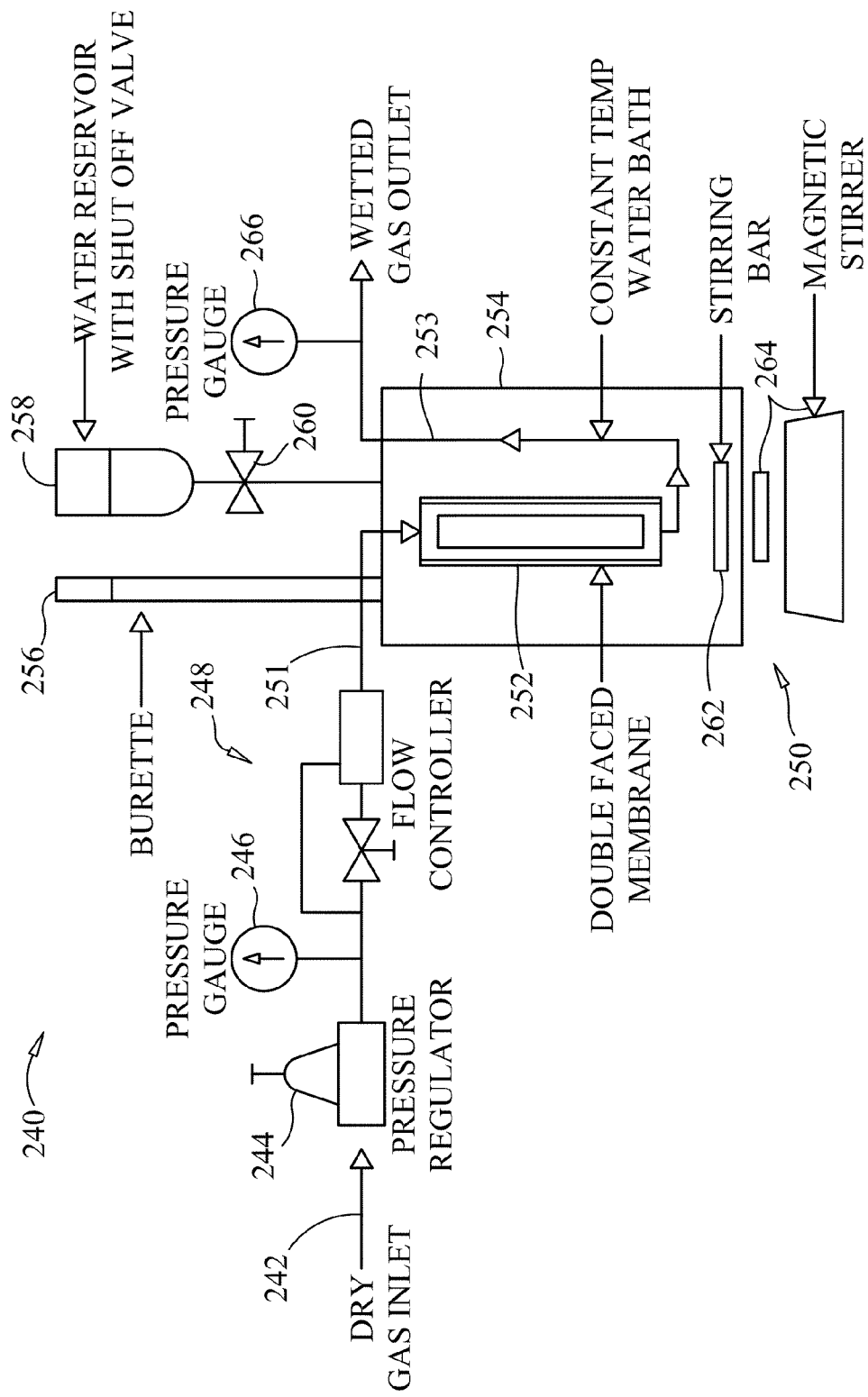
FIG. 8 is a diagram of a system for humidifying gases and liquids with an ion exchange membrane water transfer assembly, in accordance with an embodiment of the present invention.

Referring now to FIG. 8, there is shown a system 240 for humidifying gases and hydrophobic liquids using a humidifier assembly in accordance with the present invention. More particularly, as is also described in connection with FIG. 13, using a device in accordance with the present invention, precision humidification of gases and hydrophobic liquids can be achieved by passing a dry gas or liquids through a thin wall ion exchange film membrane in a temperature controlled water bath. A dry gas or hydrophobic liquid sample to be humidified is introduced to the system 240 through an inlet 242. As noted previously, it is very important to control the flows and pressures in a system, such as system 240. As such, the dry sample is introduced to a pressure regulator 244 and the pressure of the outgoing sample is monitored with the pressure gauge 246. The flow of the dry sample is regulated using a flow controller 248, the output of which is provided, via the line 251, to a humidifier system 250, in accordance with one embodiment of the present invention. The humidifier system 250, like that of the system described in connection with FIG. 13, includes a humidifier device 252, immersed in a temperature controlled water bath 254. In accordance with the teachings of the present invention, the humidifier device 252 is preferably chosen to be the assembly 140 of FIG. 2, although the assembly 130 of FIG. 1 could also be used.

The humidifier device 252 includes an inlet 251 for receiving a dry sample, and an outlet 253 for outputting the humidified sample. A pressure gauge 266 can be used to measure the pressure of the outgoing, humidified sample. The humidifier device 252 is immersed in a temperature controlled water bath 254, which, in the present embodiment, is maintained at a constant temperature. A precision burette 256 is used to monitor the level of the water in the water bath 254. Water may be replaced in the water bath 254 from a water reservoir 258, which is connected to the water bath 254 through a fill valve 260. When the fill valve 260 is closed, the water level of the burette 256 will drop in relation to the drop in the water level of the water bath 254. As such, using the burrette 256, a direct calibration of the water added from the water bath 254 to the dry gas or liquid sample can be measured with high precision. Optionally, the water bath can be stirred using any desired mechanism. In one embodiment, the water in the water bath 254 is stirred using a stirring bar 262, which is magnetically linked to a stirring device 264.

Figure 9:
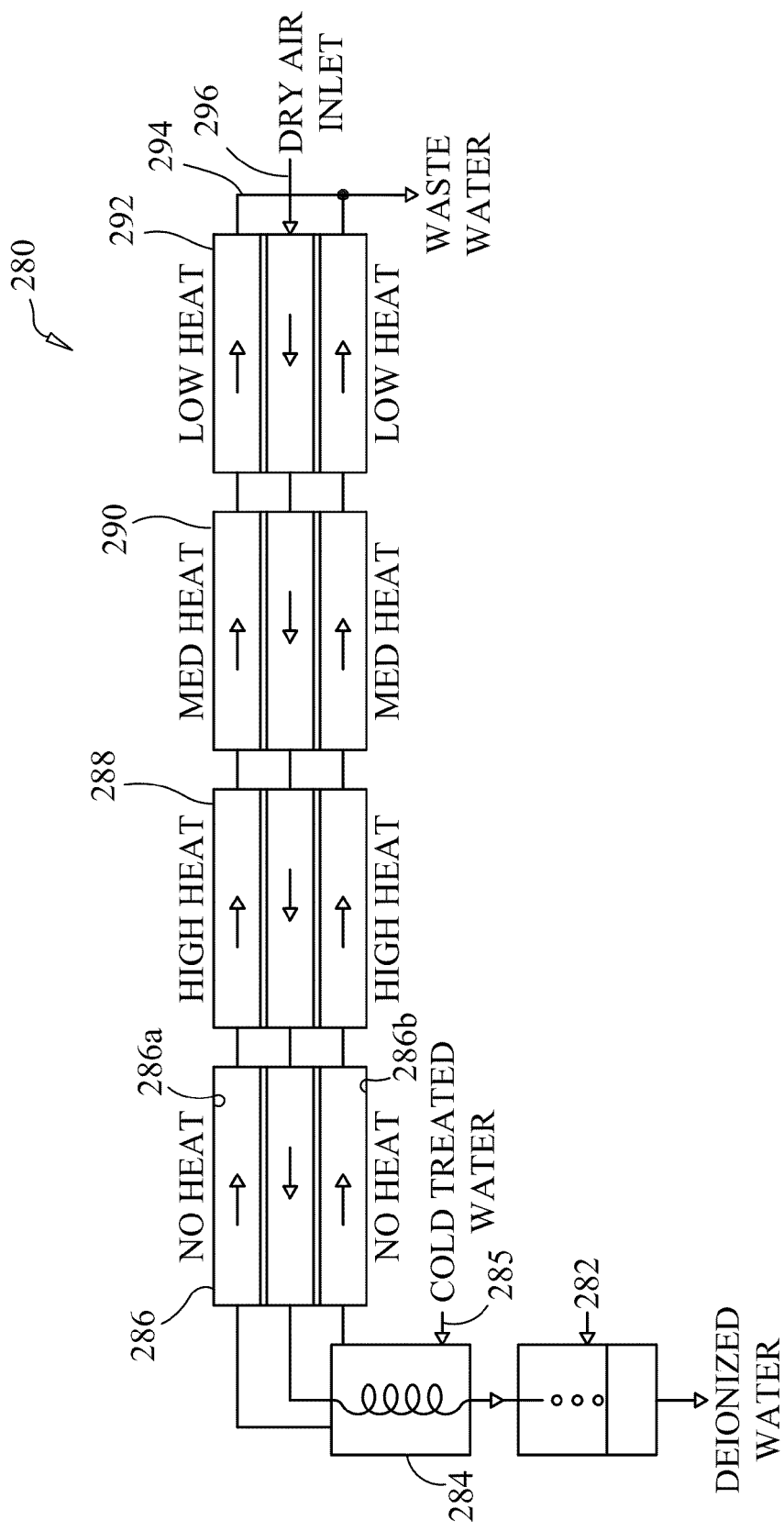
FIG. 9 is a diagram of a system for use in a large flow process application utilizing devices in accordance with an embodiment of the present invention to commercially make deionized water.

Multiple effect distillation processes are currently used to make pure water from sea water on ships and for land use. Ion exchange resins have been used in batch processes to make ion free water. Referring now to FIG. 9, there is shown one embodiment of a novel system 280 for use in a large flow process application utilizing devices in accordance with the present invention. The system 280 can be used in a commercial setting, using plant waste heat and a multiple effect distillation process to commercially make deionized water.

The system 280 of FIG. 9 uses cold, pretreated water that has been filtered and treated to remove heavy metal ions and passes the treated water over cooling coils to condense water in the saturated (humidified) gas. The deionized water resulting from the process collects in a container 282 and the carrier gas can be recycled or exhausted. Cold, pretreated water is provided to a heater 284 through an inlet 285. The water is heated and passed into a membrane evaporator 286, in accordance with the present invention. the membrane evaporator can be configured like the dryer 150 of FIG. 3. However, instead of drying a sample, the membrane evaporator 286 is used to humidify the incoming gas from dry air inlet 192, which travels through a series of membrane evaporators 286, 288, 290, 292. The heated water flows through channels 286*a* and 286*b* of the membrane evaporator 286 to humidify the air through the center chamber, which is separated from the channels 286*a* and 286*b* by membranes, as described in accordance with previous embodiments of the present invention.

During the process of system 280, no outside heat is applied to the membrane evaporator 286, however, the water membrane evaporator 286 receives heat from the saturated gas exiting from a membrane evaporator 288. In membrane evaporator 288, maximum heat is applied. The heated water exiting membrane evaporator 288 passes into another membrane evaporator 290, where medium heat is applied. The water from the membrane evaporator 290 passes through a membrane evaporator 292 under low heat, and leaves the system 280 through the waster water outlets 294. The dry or recycled air initially enters the system 280 from an inlet 296 to the membrane evaporator 292. Waste water flows through the evaporators 286, 288, 290 and 292 countercurrent to the dry air from the inlet 296. The membrane evaporators 288, 290 and 292 can be configured as described in connection with the membrane evaporator 286. Additionally, although four evaporator stages 286, 288, 290 and 292 are shown, this is not meant to be limiting, as more or fewer stages may be used, if desired. As noted above, the deionized water is separated from the saturated gas and collected in the container 282.

The system 280 of FIG. 9 requires a balance between heat input, which is the driving force for vaporizing water or saturating the dry gas. The energy requirements include the calories needed to heat the water and overcome the cooling produced by the evaporation of water (latent heat of vaporization). It offers a potential energy efficient continuous process for preparing deionized water, different from and in contrast to existing batch methods of using ion exchange resins.

Figure 10:
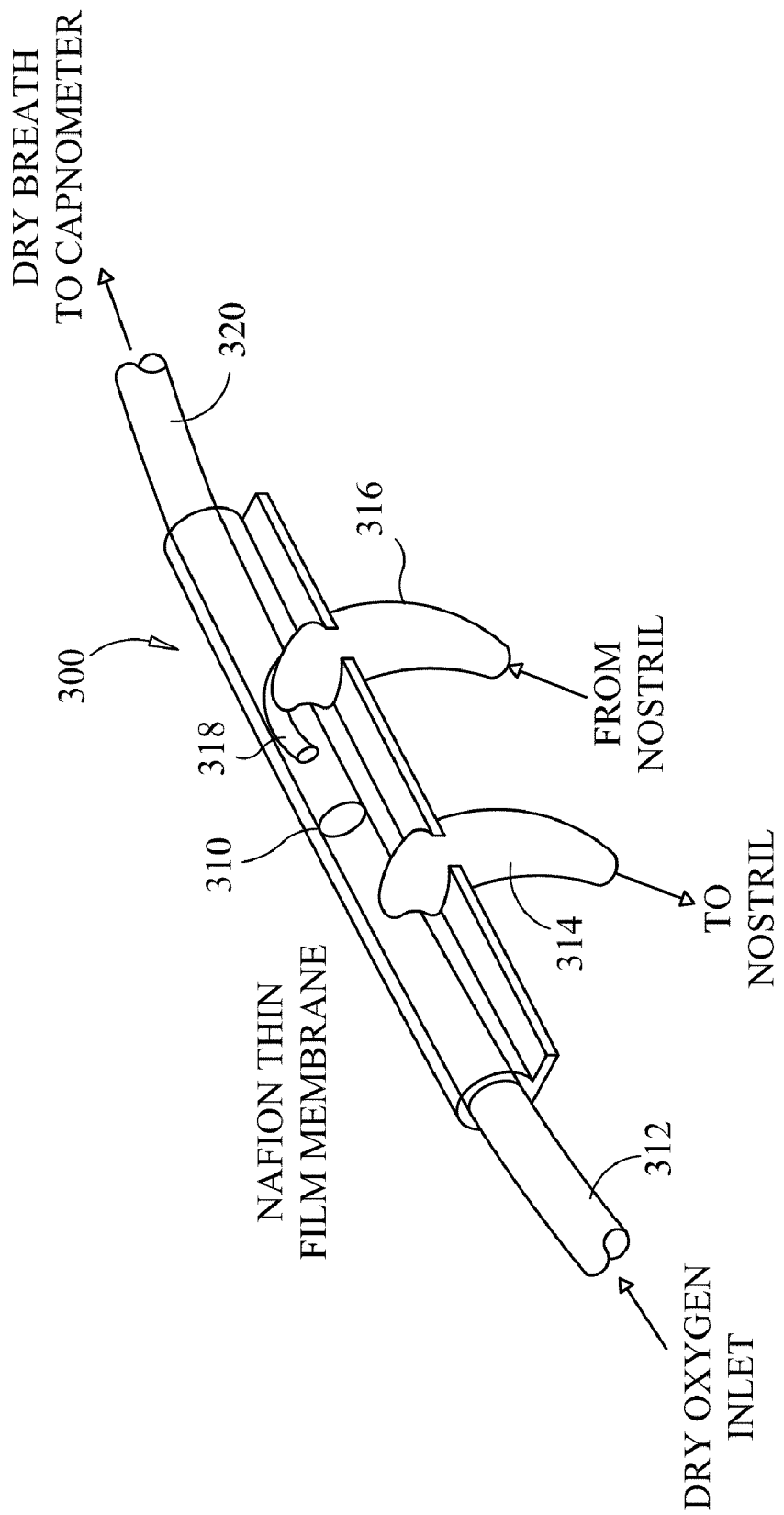
FIG. 10 shows one particular application of a water transport assembly of one embodiment of the instant application.
Figure 11:
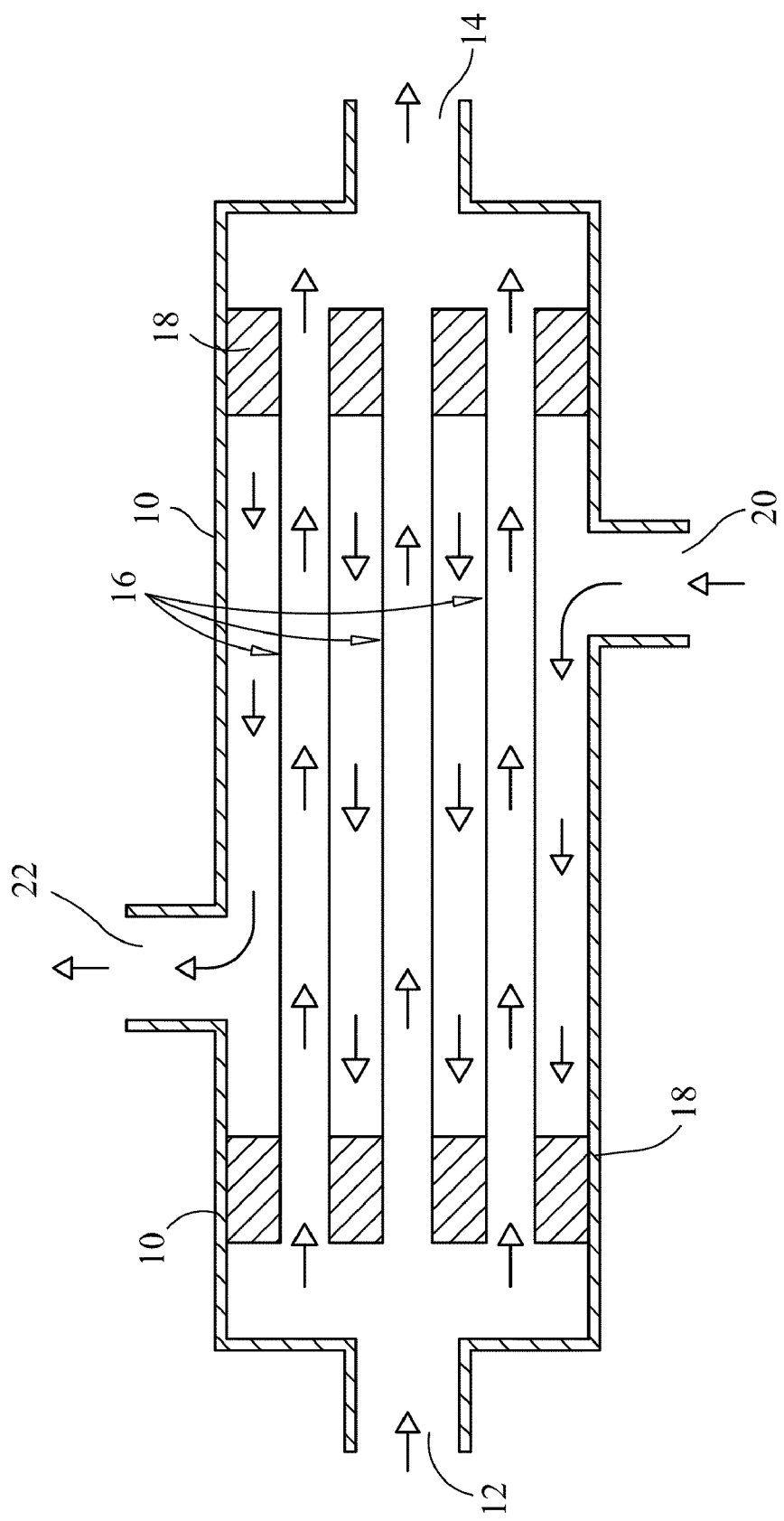
FIG. 11 is a partial cross-sectional view of a dryer including bundles of ion exchange tubes in accordance with the prior art.

Referring now to FIG. 10, there is shown one particular application of a dryer/humidifier assembly in accordance with the present invention. U.S. Pat. No. 5,335,656 to Bowe, et al., discloses a method and apparatus for inhalation of treating gas and sampling of exhaled gas for quantitative analysis. U.S. Pat. No. 5,335,656 ("the '656 patent") to Bowe, et al., is hereby incorporated herein by reference, in its entirety. FIG. 10 shows a modification that can be made to the system of the '656 patent, in accordance with the teachings of the present invention, in order to formulate a special medical dryer device that can be used for outpatient monitoring. In the '656 patent, a breath sampling unit can include an inert plastic barrier separating the oxygen inlet flow and diverting the oxygen inlet into one nostril of a patient. The exhaust breath from the other nostril is blocked by the barrier and passes into the breath sample line to the capnometer. Using the present invention in connection with a system such as disclosed in the '656 patent, as shown in FIG. 10, the inert plastic barrier in the cannula 300 of the '656 patent can be replaced by a thin ion exchange film membrane 310 of the sulfonic acid type, preferably in its hydrogen form, such as a NAFION® membrane, i.e., a perfluorosulfonic acid membrane, or a membrane of another type, as disclosed above. As such, a flat, thin ion exchange film membrane will be arranged in the inner passageway of the cannula, so as to block the flow of gases from one portion of the cannula, to the other. In one embodiment, the flat thin ion exchange film membrane is located in the cannula relatively perpendicular to the length of the cannula. The dry oxygen ported into the cannula 300 will additionally remove water that is adsorbed from the exhaust breath. More particularly, dry oxygen will come into the cannula through the dry oxygen inlet tube 312 and enter one of the patient's nostrils, through the nostril tube 314. A wet exhalation gas will enter the cannula from the second nostril tube 316, when the patient exhales.

In accordance with the teachings of the present invention, the dry oxygen gas flowing past the membrane 310 exceeds the wet patient exhaust breath flow and the thin film membrane is used to dry the patient's breath, prior to transport to a capnometer. When the patient exhales, the moist exhalation breath from the second nostril tube 316, is channeled by a restricted diameter tube 318, towards the membrane 310. As noted above, the flow of dry oxygen against one side of the membrane 310 draws the water from the moist exhalation breath from tube 318, through the membrane 310. As such, dried patient breath flows out of the output tube 320 to a capnometer (not shown).

It can be seen from the foregoing, that devices made in accordance with the present invention overcome many of the limitations of the prior art systems. Advantageously, in a thin film dryer systems in accordance with the present invention, the entire film membrane is exposed to the wet sample and dry purge gas, in contrast to multi-tube dryers in which the tubes can readily cover each other and reduce the contact of purge gas with the tubing. Dryers including thin ion exchange film membranes, in accordance with the present invention, thus demonstrate faster transport rates of water through the membrane. Additionally, devices made in accordance with the present invention are very economical and maintain their chemical inertness throughout their use. Further, certain devices in accordance with the present invention can be further used to efficiently and cost effectively humidify a dry sample. Such humidification systems can be used to saturate hydrogen for fuel cells and/or to saturate recycled patient breath in medical and related applications.

I claim:

1. A water transport assembly, comprising:
a first evaporator including:
a first housing including a first chamber, a sample inlet port and a sample outlet port, both of said ports being in fluid communication with said first chamber;
a first flat thin ion exchange membrane of the sulfonic acid type attached to said housing in a plane over said first chamber to seal said first chamber in a vapor tight seal;
said first flat thin ion exchange membrane being between about 0.1 and about 3.0 mils in thickness;
a second evaporator including:
a second housing including a second chamber, a second sample inlet port and a second sample outlet port, both of said ports being in fluid communication with said second chamber;
a second flat thin ion exchange membrane of the sulfonic acid type attached to said housing in a plane over said second chamber to seal said second chamber in a vapor tight seal;
said second flat thin ion exchange membrane being between about 0.1 and about 3.0 mils in thickness;
said first evaporator and said second evaporator connected to one another in a multiple effect evaporator configuration.

2. The water transport assembly of claim 1, wherein said first flat thin ion exchange membrane is formed with a perfluorosulfonic acid polymer.

3. The water transport assembly of claim 2, wherein said first flat thin ion exchange membrane is made using a thin film cast from a perfluorosulfonic acid polymer.

4. The water transport assembly of claim 2, wherein said first flat thin ion exchange membrane is formed by a dispersion of perfluorosulfonic acid polymer.

5. The water transport assembly of claim 1, wherein said first flat thin ion exchange membrane is in the hydrogen (H+) form.

6. The water transport assembly of claim 1, wherein said first housing additionally includes a third chamber and said water transport assembly additionally including a third flat thin ion exchange membrane attached to said housing in a plane over said third chamber to seal said second third chamber in a vapor tight seal, and wherein said third flat thin ion exchange membrane is between about 0.1 and about 3.0 mils in thickness.

7. The water transport assembly of claim 6, wherein at least one of said first flat thin ion exchange membrane and said second flat thin ion exchange membrane is formed with a perfluorosulfonic acid polymer.

8. The water transport assembly of claim 1, including a purge chamber located above said first flat thin ion exchange membrane.

9. The water transport assembly of claim 8, wherein said purge chamber includes a purge gas inlet in fluid communication with said purge chamber and a purge gas outlet in fluid communication with said purge chamber.

10. The water transport assembly of claim 6, including a first purge chamber located above said first flat thin ion exchange membrane and a second purge chamber located above said second flat thin ion exchange membrane.

11. The water transport assembly of claim 10, wherein said purge chamber includes a purge gas inlet in fluid communication with at least said first purge chamber and a purge gas outlet in fluid communication with at least said first purge chamber.

12. The water transport assembly of claim 11, wherein at least one of said first flat thin ion exchange membrane and said second flat thin ion exchange membrane is formed with a perfluorosulfonic acid polymer.

13. A humidification system, comprising:
a humidifier assembly, including:
a housing including a first chamber, said first chamber being accessible through an opening in said housing, said housing additionally including a sample inlet port and a sample outlet port, both of said ports being in fluid communication with said first chamber;
a first flat thin ion exchange membrane of the sulfonic acid type attached to said housing in a plane over said opening to seal said opening in a vapor tight seal;
said first flat thin ion exchange membrane being between about 0.1 and about 3.0 mils in thickness; and
said housing additionally includes a second chamber, said second chamber being accessible through a second opening in said housing, said humidifier assembly additionally including a second flat thin ion exchange membrane attached to said housing in a plane over said second opening to seal said second opening in a vapor tight seal, and wherein said second flat thin ion exchange membrane is between about 0.1 and about 3.0 mils in thickness; and
a temperature controlled water bath containing said humidifier assembly.

14. The humidification system of claim 13, wherein at least one of said first flat thin ion exchange membrane and said second flat thin ion exchange membrane is formed with a perfluorosulfonic acid polymer.

15. A dryer system, comprising:
a dryer assembly, including:
a housing including a first chamber, a sample inlet port and a sample outlet port, both of said ports being in fluid communication with said first chamber;
a first flat thin ion exchange membrane of the sulfonic acid type being located in a plane over the first chamber of the housing in a vapor tight seal;
said first flat thin ion exchange membrane being between about 0.1 and about 3.0 mils in thickness; and
a temperature control mechanism for adjusting the temperature of the dryer assembly to produce a dried sample at the sample outlet port, said temperature control mechanism being adjustable to reduce the liquid content of the dried sample.

16. The dryer system of claim 15, including a purge chamber located above said first flat thin ion exchange membrane.

17. The dryer system of claim 16, wherein said housing additionally includes a second chamber and said dryer additionally including a second flat thin ion exchange membrane attached to said housing in a plane over said second chamber to seal said second chamber in a vapor tight seal, and wherein said second flat thin ion exchange membrane is between about 0.1 and about 3.0 mils in thickness.

18. The dryer system of claim 17, wherein at least one of said first flat thin ion exchange membrane and said second flat thin ion exchange membrane is formed with a perfluorosulfonic acid polymer.

19. The dryer system of claim 17, including a plurality of said dryer assemblies aligned in parallel.

20. The dryer system of claim 19, including a plurality of purge gas chambers, at least one purge gas chamber being located between each two membranes of said plurality of dryer assemblies.

21. A method for drying a wet sample, comprising the steps of:
providing a dryer assembly, including:
a housing including a first chamber, a sample inlet port and a sample outlet port, both of the ports being in fluid communication with the first chamber;
a first flat thin ion exchange membrane of the sulfonic acid type being located in a plane over the first chamber of the housing in a vapor tight seal;
the first flat thin ion exchange membrane being between about 0.1 and about 3.0 mils in thickness;
providing the wet sample to the sample inlet port;
recovering a dried sample from the sample outlet port; and
adjusting the temperature of the dryer assembly to reduce the liquid content in the dried sample.

22. The method of claim 21, further including the step of providing a purge gas in communication with one side of the first flat thin ion exchange membrane, to draw moisture from the wet sample through the first flat thin ion exchange membrane.

23. The method of claim 21, wherein the providing a dryer assembly step includes providing a plurality of dryer assemblies connected in parallel.

24. The method of claim 21, wherein the housing additionally includes a second chamber, and the dryer assembly additionally includes a second flat thin ion exchange membrane attached to the housing in a plane over the second chamber in a vapor tight seal, and wherein the second flat thin ion exchange membrane is between about 0.1 and about 3.0 mils in thickness.

25. The method of claim 24, wherein at least one of the first flat thin ion exchange membrane and the second flat thin ion exchange membrane is formed with a perfluorosulfonic acid polymer.

26. A method of humidifying a gas, comprising the steps of:
providing a humidifier assembly, including:
a housing including a first chamber, the first chamber being accessible through an opening in the housing, the housing additionally including a sample inlet port and a sample outlet port, both of the ports being in fluid communication with the first chamber;
a first flat thin ion exchange membrane of the sulfonic acid type attached to the housing in a plane over the opening to seal the opening in a vapor tight seal;
the first flat thin ion exchange membrane being between about 0.1 and about 3.0 mils in thickness;
the housing additionally including a second chamber, the second chamber being accessible through a second opening in the housing, the humidifier assembly additionally including a second flat thin ion exchange membrane attached to the housing in a plane over the second opening to seal the second opening in a vapor tight seal, and wherein the second flat thin ion exchange membrane is between about 0.1 and about 3.0 mils in thickness;
immersing the humidifier assembly in a temperature controlled water bath;
providing a dry sample to the sample inlet port; and
recovering a humidified sample from the sample outlet port.

27. The method of claim 26, wherein at least one of the first flat thin ion exchange membrane and the second flat thin ion exchange membrane is formed with a perfluorosulfonic acid polymer.

28. A medical device including a water transport assembly, the medical device comprising:
a cannula having an inner passageway, said cannula including:
a first nostril tube located at a first position along said cannula;
a second nostril tube located at a second position along said cannula;
a thin ion exchange film membrane of the sulfonic acid type, being located across said inner passageway, between said first position and said second position, so as to block the flow of gasses through said inner passageway from said first position to said second position.

29. The medical device of claim 28, further including a restricted diameter tube in communication with one of said first nostril tube and said second nostril tube, to direct a gas from said nostril tube towards said thin ion exchange film membrane.

30. The medical device of claim 28, further including:
a capnometer connected to said cannula, proximal said second position; and
a gas source connected to said cannula, proximal to said first position.

31. A method of drying a patient's breath, comprising:
providing a cannula having an inner passageway, the cannula including:
a first nostril tube located at a first position along the cannula;
a second nostril tube located at a second position along the cannula;
a thin ion exchange film membrane of the sulfonic acid type, being located across the inner passageway, between the first position and the second position, so as to block the flow of gasses through the inner passageway from the first position to the second position;
positioning in communication with the patient, such that the first nostril tube is in one of the patient's nostrils, and the second nostril tube is in the patient's second nostril;
providing a first gas to the cannula, proximal to the first position;
receiving into the inner passageway of the cannula, a second gas from the second nostril tube;
removing a dried second gas from the cannula, proximal to the second position; and
the first gas containing less moisture than the second gas, in order to draw moisture from the second gas through the thin ion exchange film membrane to produce the dried second gas.

32. The method of claim 31, wherein the first gas is a dry, oxygen containing gas, and the dried second gas is provided to a capnometer for analysis.

33. The water transport assembly of claim 1, further including at least a third evaporator configured as a multiple effect evaporator with said first evaporator and said second evaporator.

34. The water transport assembly of claim 1, wherein said multiple effect evaporator produces deionized water at an output of the multiple effect evaporator.

35. The water transport assembly of claim 1, further including a temperature control mechanism for applying heat to the second evaporator.

36. The water transport assembly of claim 1 wherein steam produced in said second evaporator assembly is used to heat said first evaporator assembly.

37. The dryer system of claim 15, wherein the temperature control mechanism adjusts the temperature of the dryer assembly to dry the sample to a liquid level of no more than a few parts per million.

38. The method of claim 21, wherein adjusting step adjusts the temperature of the dryer assembly to dry the sample to a liquid level of no more than a few parts per million.

* * * * *